United States Patent [19]

Pedrazzi

[11] 4,126,608
[45] Nov. 21, 1978

[54] PROCESS FOR THE PRODUCTION OF SALTS OF STILBENE-AZO AND STILBENE-AZOXY DYES

[75] Inventor: Reinhard Pedrazzi, Basel, Switzerland

[73] Assignee: Fidelity Union Trust Company as Executive Trustee under the Sandoz Trust, Newark, N.J.

[21] Appl. No.: 641,484

[22] Filed: Dec. 17, 1975

Related U.S. Application Data

[60] Division of Ser. No. 385,756, Aug. 6, 1973, Pat. No. 3,953,419, which is a continuation-in-part of Ser. No. 338,321, Mar. 5, 1973, abandoned, and a continuation-in-part of Ser. No. 338,339, Mar. 5, 1973, abandoned.

[30] Foreign Application Priority Data

Mar. 17, 1972 [CH] Switzerland .......................... 4042/72
Aug. 8, 1972 [CH] Switzerland ........................ 11699/72
Mar. 9, 1972 [CH] Switzerland .......................... 1477/72

[51] Int. Cl.² .............................................. C09B 27/02
[52] U.S. Cl. .................................... 260/143; 260/169; 260/205
[58] Field of Search ........................ 260/143, 169, 205

[56] References Cited

U.S. PATENT DOCUMENTS 3,547,774 12/1970 Rebhahn .......................... 260/205 X
3,905,949 9/1975 Perkins et al. .................... 260/169 X

FOREIGN PATENT DOCUMENTS 1,114,944 5/1968 United Kingdom ..................... 260/143

Primary Examiner—Charles F. Warren
Attorney, Agent, or Firm—Gerald D. Sharkin; Richard E. Vila; Melvyn M. Kassenoff

[57] ABSTRACT

Salts of stilbene-azo and stilbene-azoxy dyestuffs, and mixtures thereof in which the cations are selected from tetra-alkylammonium, tetraalkylammonium in combination with lithium, sodium, potassium or ammonium, and ammonium in combination with lithium, sodium or potassium, have good cold water solubility relative to known salts of such dyes.
The preferred dyes have the formula

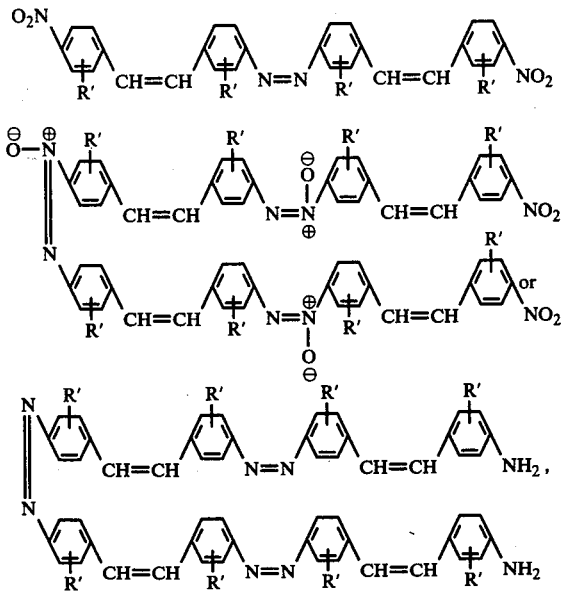

wherein
(1) each R' is independently —SO₃⁻M⁺ or —SO₃⁻N⁺(R)₄,
wherein each R is independently alkyl of 1 to 6 carbon atoms or alkyl of 1 to 6 carbon atoms substituted by hydroxy, cyano, halo or phenyl, and
each M⁺ is independently hydrogen, lithium, sodium, potassium or ammonium, with the proviso that at least one R' is —SO₃⁻N⁺(R)₄,
(2) each R' is —SO₃⁻M⁺,
wherein each M⁺ is lithium, sodium, potassium, or ammonium, with the proviso that at least one M⁺ is ammonium, or
(3) each R' is independently —SO₃⁻M⁺ or —SO₃⁻N⁺(R)₄,
wherein each R is independently alkyl of 1 to 6 carbon atoms or alkyl of 1 to 6 carbon atoms substituted by hydroxy, cyano or halo, and
each M⁺ is ammonium or an alkali metal, with the proviso that at least one R' is —SO₃⁻M⁺ wherein M⁺ is ammonium.

The dyes are useful for producing colored paper by incorporation into paper stock or by application to paper sheet. The dyed paper is fast to light and wet treatments.

25 Claims, No Drawings

PROCESS FOR THE PRODUCTION OF SALTS OF STILBENE-AZO AND STILBENE-AZOXY DYES

This application is a division of application Ser. No. 385,756, filed Aug. 6, 1973 and now U.S. Pat. No. 3,953,419, which is a continuation-in-part of application Ser. No. 338,321, filed Mar. 5, 1973 and now abandoned, and application Ser. No. 338,339, filed Mar. 5, 1973 and now abandoned.

The invention provides novel salts of a stilbene-azo or stilbene-azoxy dye containing at least one sulphonic acid group per molecule, in which any cation is selected from tetra (substituted or unsubstituted) alkylammonium, tetra (substituted or unsubstituted) alkylammonium in combination with lithium, sodium, potassium or ammonium, and ammonium in combination with lithium, sodium or potassium.

The invention also provides various processes for the production of such salts.

Thus, for example, a salt of a stilbene-azo or stilbene-azoxy dye containing at least one sulphonic acid group per molecule, in which at least one cation per molecule is a tetra (substituted or unsubstituted alkyl) ammonium cation, may be prepared by a process which comprises condensing a compound of formula I,

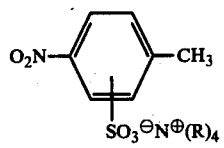

in which R signifies a substituted or unsubstituted alkyl radical, in the presence of a tetra (substituted or unsubstituted alkyl ammonium hydroxide to form a stilbene-azo or stilbene-azoxy dye in salt form and, if desired, reducing the resulting dye to convert the nitro groups to amino groups.

The alkyl radical R may be primarily a lower alkyl radical which contains 1 to 6 or preferably 1 2 carbon atoms. If the alkyl radical is substituted it may contain preferably a hydroxyl or cyano group or a halogen atom or an aryl radical, advantageously a phenyl radical.

It is preferred to use a molar excess of the tetraalkylammonium hydroxide. It is preferred to begin with the compound of formula I in free sulphonic acid form rather than in salt form and add it to a molar excess of the tetraalkylammonium hydroxide so that the salt form of the compound of formula I is formed in situ. Accordingly, it is preferred that the cation in the compound of formula I corresponds to the tetraalkylammonium hydroxide. The reaction is preferably effected in aqueous medium, suitably at a pH of from 7.5 to 14, especially 11 to 13. The reaction is preferably carried out at elevated temperatures, suitably from 30° C. to the boiling temperature of the reaction mixture, especially from 45° to 70° C. Under preferred conditions the reaction time is from 15 minutes to 2 hours. The reaction generally results in a mixture of salts, which if desired can be separated in conventional manner. When it is desired to reduce the resulting dye salt to form the primary amino derivative, this can be effected in conventional manner, for example in aqueous solution in the presence of dextrose hydrate, an alkali metal sulphite or sulphide, glycerin, a hydroxyalkylamine or an aldehyde, for example sodium sulphite or sulphide, hydroxymethylamine or acetaldehyde.

If desired, the salts produced according to the process of the invention can be converted into salts of a stilbene-azo or stilbene-azoxy dye in which at least one cation on a sulphonic acid group per molecule is a tetraalkylammonium cation and any other sulphonic acid group in the molecule is in the form of an alkali metal or ammonium salt by reacting the product of the process with an alkali metal salt and/or ammonium salt. The formation of such lithium, sodium, potassium or ammonium salts may be carried out in conventional manner, for example with a halide, especially the chloride, sulphate, acetate or phosphate of such cations. The reaction is preferably effected in aqueous medium, preferably at elevated temperatures such as 50° to 100° C., preferably 70° to 85° C.

The salts according to this invention are of Formulae II, IV and VI

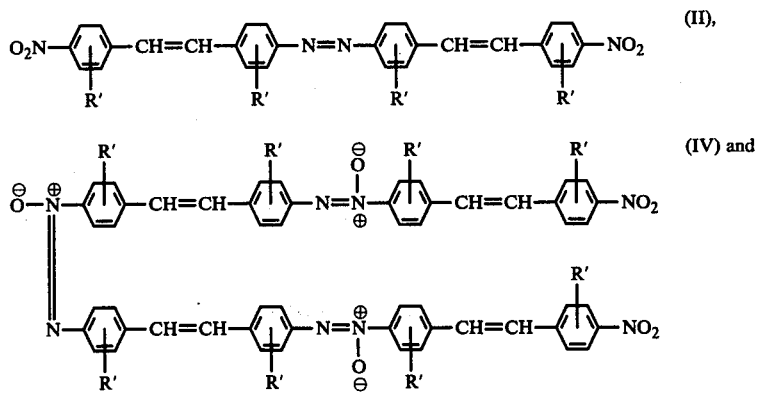

-continued

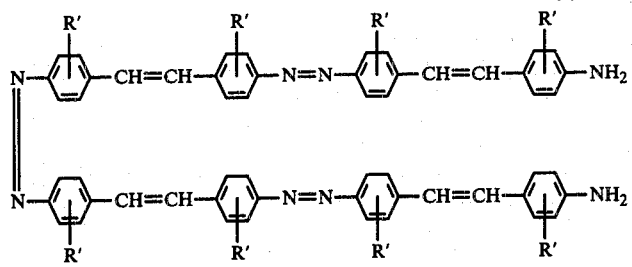 (VI), wherein each R' is independently —SO₃⁻M⁺ or —SO₃⁻N⁺(R)₄, wherein each R is independently alkyl of 1 to 6 carbon atoms or monosubstituted alkyl of 1 to 6 carbon atoms wherein the substituent is hydroxy, cyano, chloro, bromo or phenyl, and each M⁺ is independently hydrogen, lithium, sodium, potassium, or ammonium, with the proviso that at least one R' is —SO₃⁻N⁺(R)₄.

Preferably, each R is alkyl of 1 or 2 carbon atoms or monosubstituted alkyl of 1 or 2 carbon atoms; more preferably, each R is methyl.

Particularly preferred salts according to the invention are of formula II,

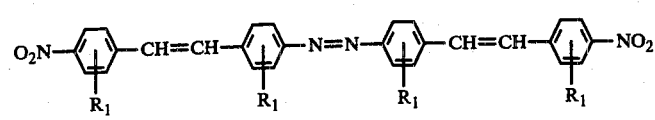

in which each $R_1$ signifies —SO₃H or —SO₃⁻(CH₃)₄N⁺ and the molecule contains at least one tetramethylammonium cation; salts of formula III,

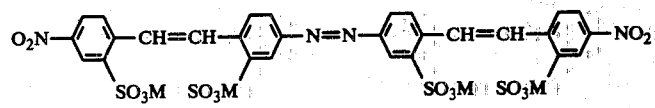

in which each M signifies hydrogen or a tetramethylammonium cation and the dye molecule contains at least one tetramethylammonium cation; salts of formula IV,

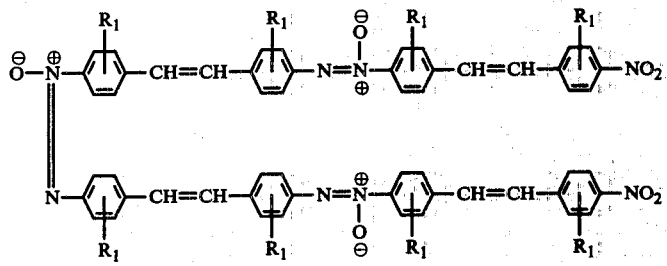

in which each $R_1$ signifies —SO₃H or —SO₃⁻(CH₃)₄N⁺ and the molecule contains at least one tetramethylammonium cation;

salts of formula V,

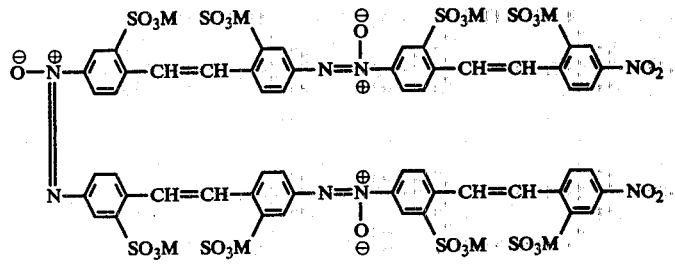

in which each M signifies hydrogen or a tetramethylammonium cation and the dye molecule contains at least one tetramethylammonium cation; salts of formula VI,

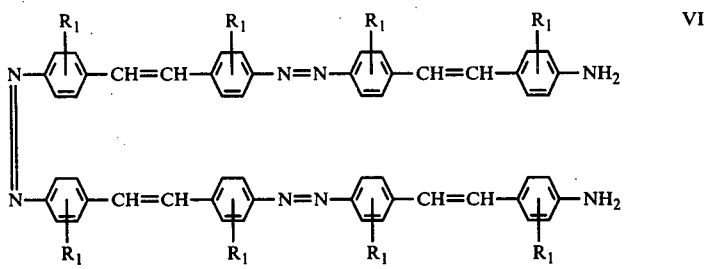

in which $R_1$ signifies —$SO_3H$ or —$SO_3^{\ominus}(CH_3)_4N^{\oplus}$ and the molecule contains at least one tetramethylammonium cation;

salts of formula VII,

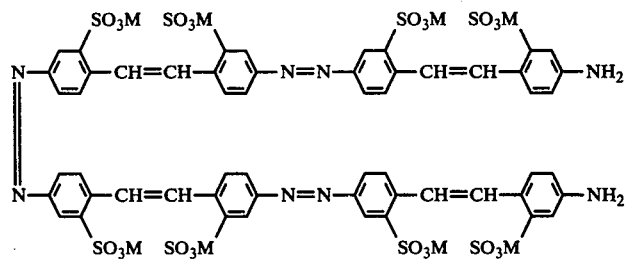

in which each M signifies hydrogen or a tetramethylammonium cation and the dye molecule contains at least one tetramethylammonium cation.

Dyes of formulae II to VII can be produced in accordance with the process of this invention. Mixtures of dyes of formulae II to VII also can be produced.

The invention also comprises in particular salts of formula VIII,

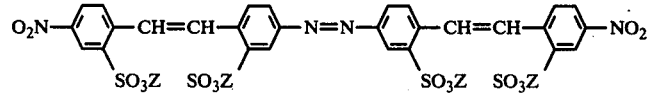

in which each Z signifies Li, Na, K, —$N^{\oplus}H_4$ or —$N^{\oplus}(CH_3)_4$ and the molecule contains at least one —$N^{\oplus}(CH_3)_4$ cation;

salts of formula IX,

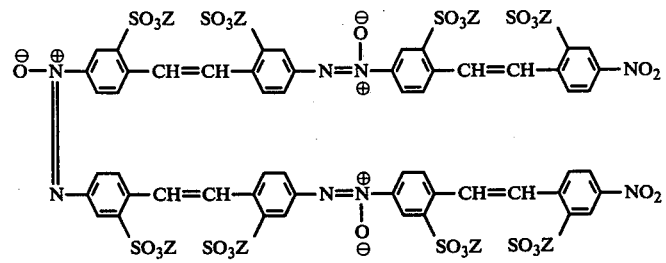

in which each Z signifies Li, Na, K, —$N^{\oplus}H_4$ or —$N^{\oplus}(CH_3)_4$ and the molecule contains at least one —$N^{\oplus}(CH_3)_4$ cation;

salts of formula X,

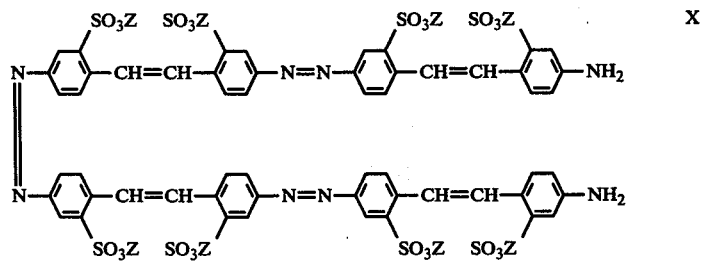

in which each Z signifies Li, Na, K, —$N^{\oplus}H_4$ or —$N^{\oplus}(CH_3)_4$ and the molecule contains at least one —$N^{\oplus}(CH_3)_4$ cation.

Mixtures of dyes of formula VIII to X also can be produced.

The dyes of formula III, V and VII in the form of the lithium salts are disclosed in British Patent No. 1,114,944. They are used for paper dyeing.

Also, a salt of a stilbene-azo or stilbene-azoxy dye containing at least one sulphonic acid group per molecule, in which at least one cation per molecule is an ammonium cation, any remaining cation being a lithium cation, may be prepared by a process which comprises reacting a lithium salt of a stilbene-azo or stilbene-azoxy dye containing at least one sulphonic acid group per molecule with an ammonium salt. The process may conveniently be effected using mixtures of lithium salts of different dyes, thus producing mixtures of dye salts according to the invention.

This process of the invention may be carried out using an ammonium salt such as ammonium chloride, sulphate, acetate or phosphate. The reaction is preferably effected in aqueous medium which is suitably neutral or weakly acidic or weakly basic, e.g. preferably in the pH range 6.5 to 7.5 and is preferably carried out at an elevated temperature, e.g. from 50° to 100° C., especially from 70° to 85° C. Reaction times under preferred conditions are usually from 15 minutes to 2 hours.

Particularly preferred dye salts according to the invention are of formulae Ia, IIa and IIIa,

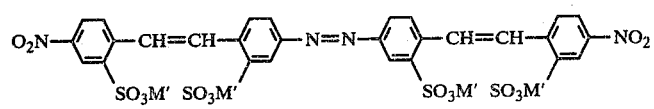

Ia in which each M' signifies a lithium cation or $NH_4^{\oplus}$ and the dye molecule contains at least one $NH_4^{\oplus}$ cation;

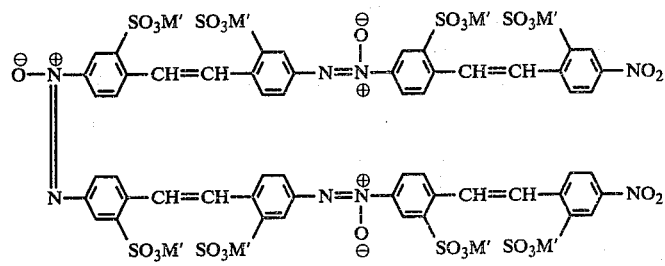

in which M' is as defined above,

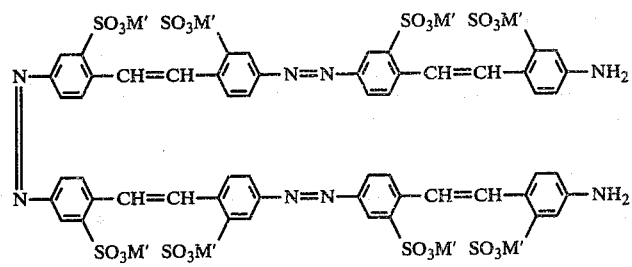

in which M' is as defined above.

Mixtures of dye salts of formulae Ia, IIa or IIIa in particular are included within the scope of the invention.

Further, the invention provides a process for the production of a salt of a stilbene-azo or stilbene-azoxy dye containing at least one sulphonic acid group per molecule, in which at least one cation per molecule is an ammonium cation, any other cation being selected from tetra (substituted or unsubstituted) alkylammonium and alkali metal cations, which comprises condensing a compound of formula Ib,

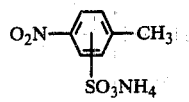

Ib in the presence of an alkali metal hydroxide or a tetra (substituted or unsubstituted) alkylammonium hydroxide. If desired, simultaneous or subsequent reduction may also be carried out, thus forming a dye salt with a primary amino group or groups.

The process of the invention is preferably effected in an aqueous medium, suitably at a pH of from 7.5 to 14, especially 11 to 13. The process is preferably carried out in the presence of water (as the solvent) at a pH of 11 to 14. The reaction is preferably effected above room temperature, conveniently at from 30° to 75° C., preferably at 45° to 65° C. Under the preferred conditions, reaction times are usually from about 1 to 12 hours. The alkyl radicals in the tetraalkylammonium hydroxide may be primarily a lower alkyl radical, of 1 to 6 or more preferably of 1, 2 or 3 carbon atoms, and if substituted, is preferably monosubstituted by cyano, halogen, preferably chlorine or bromine, or hydroxyl. Sodium, potassium and preferably, lithium hydroxide are suitable alkali metal hydroxides, and the preferred tetraalkylammonium hydroxide is tetramethylammonium hydroxide. The amount of hydroxide used may vary according to other reaction parameters such as temperature and reaction time but is generally in a molar range of 0.5 to 6 mols, preferably in the range of 0.8 to 4 mols, per mol of compound of formula Ib.

The reduction reaction may be effected in conventional manner, for example using dextrose hydrate, glycerin, glucose, sugar, an alkali metal sulphite or sulphide, a hydroxyalkylamine or an aldehyde, preferably an alkyl aldehyde such as acetaldehyde. The amount of reducing agent also varies, but is influenced primarily by the strength of the reducing agent and the reaction time.

Preferred products of this process of the invention are:

compounds of formula IIb,

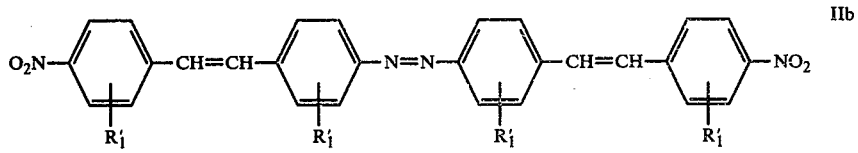

in which $R_1'$ signifies —$SO_3H$ in the form of the ammonium, tetra (substituted or unsubstituted) alkylammonium or alkali metal salt and at least one —$SO_3H$ group is present in the form of the ammonium salt, or preferably compounds of formula IIIb,

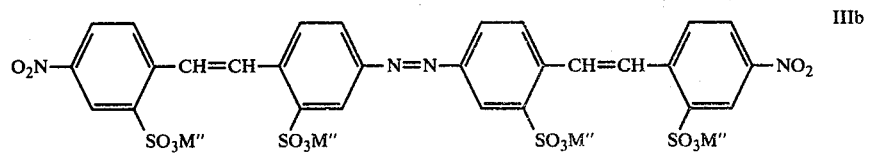

in which each M" signifies an alkali metal cation or a tetraalkylammonium cation or an ammonium cation and the molecule contains at least one ammonium cation, further, compounds of formula IVb,

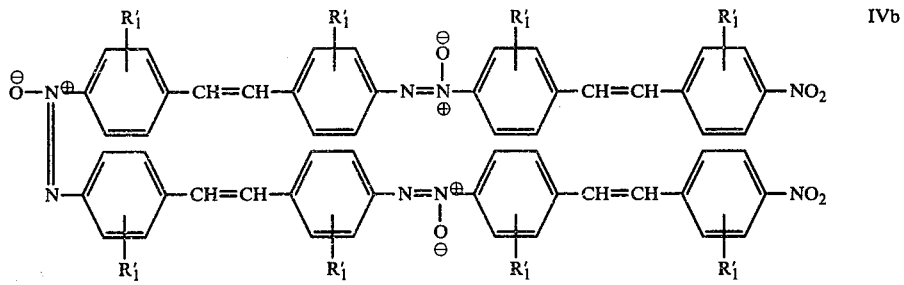

in which $R_1'$ is as defined above, or preferably compounds of formula Vb,

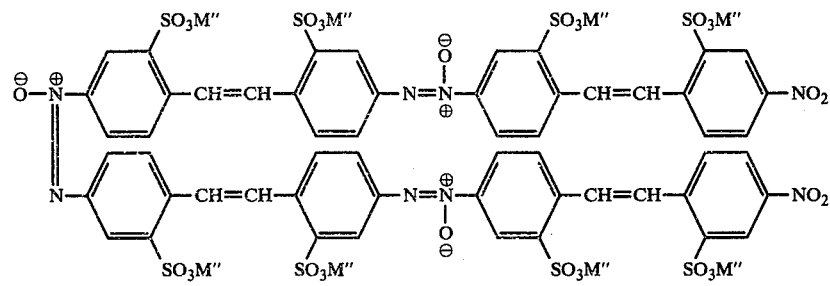

in which M" is as defined above, further, compounds of formula VIb,

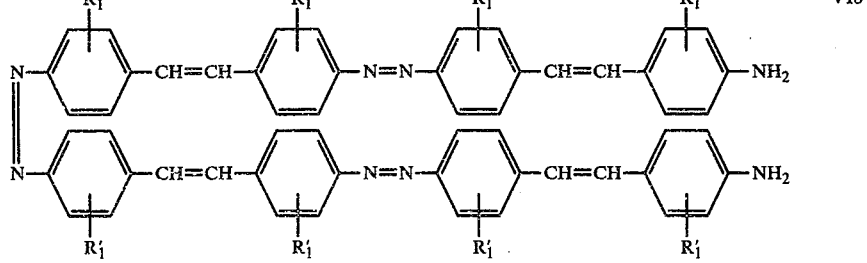

in which $R_1'$ is as defined above, or preferably compounds of formula VIIb,

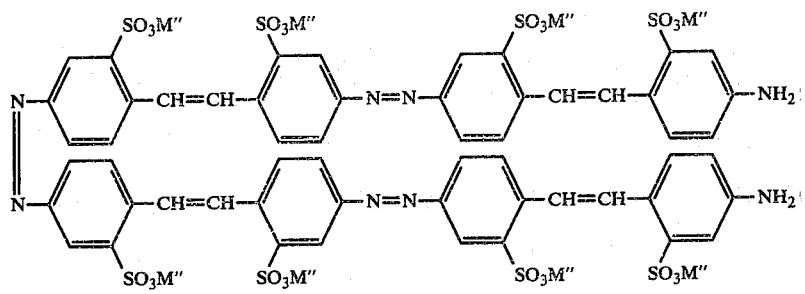

in which M″ is as defined above. Each M″ is preferably $N^{\oplus}H_4$, a tetra($C_{1-3}$alkyl)ammonium cation or an alkali metal cation, with the proviso that at least one M″ per molecule is $N^{\oplus}H_4$.

The compounds of formulae VIb and VIIb may be prepared by reduction of the corresponding nitro compounds of formulae IVb and Vb.

Mixtures of dyes of formulae II to VII also can be produced using the process of the invention. The products of the reaction indeed are mixtures of dye salts of structures IIb and IVb, which may be used as such as dyes. While the reaction may be conducted by reacting until a desired shade is reached, it is also possible to prepare a mixture having a preponderance of compound of formula IIb by condensing at about 40°–50° C. with about 0.5 to 1 mol of hydroxide per mol of compound of formula Ib, giving a pH of from 12 to 14, for about one hour. A mixture having a preponderance of compound of formula IVb by condensing at about 50° to 80° C. with about 1 to 6 mols of hydroxide per mol of compound of formula Ib, giving a pH of from 12 to 14, for about 1 to 12 hours.

The dyestuff salt produced according to the invention generally precipitates in more easily filtrable form than the product of the condensation of the lithium salt.

Surprisingly, the novel salts of these compounds have high solubility in cold water, in contrast to the conventional powder forms of the commercially available stilbene-azo dyes disclosed in the cited patent. Moreover, the new salts tend to have rather higher tinctorial strength in the dyeing of paper than the dyes of the said patent.

The dried, i.e. completely water-free, dye salts from British Pat. No. 1,114,944, in the form of the pure lithium salts, have good solubility in water but are very hygroscopic. For this reason they cannot be converted into a granulated form, or only with great difficulty. The salts of the present invention can be more easily converted into a granulated form.

A further, related advantage of the new salts is that they can be submitted to spray drying. With the dyes of the British patent this is not practicable as they are far too hygroscopic.

The new salts are suitable primarily for dyeing sized and unsized papers in the stock prior to sheet formation. They can also be used for dyeing paper by the dipping technique. The new dyes have excellent solubility properties, in particular good solubility in cold water. The degree of coloration of the backwater in paper manufacture is only slight, which is an important asset for effluent control. The dyes do not mottle or dye paper in two-sided effects, and are largely insensitive to pH conditions. The dyeings are of brilliant shade and have excellent light fastness. After a lengthy period of exposure to light the shade fades tone-in-tone. The dyed papers are generally wet fast, not only to water but also to milk, fruit juices, soft drinks and alcoholic drinks, the fastness to alcohol being generally very good.

The dyes can be added directly to the paper stock, i.e. without previous dissolving, as dry powders or granules, which does not lead to diminishment in the brilliance or loss of colour yield. By aftertreatment with cationic fixing agents almost perfect wet and alcohol fastness properties are obtained. The dyed papers are bleachable by oxidation and or reduction methods, which is important for the re-use of broke and waste paper.

The new dyes can be converted into concentrated liquid preparations, which are storable for long periods of time and owing to their storage stability are preferred for use. The production of concentrated liquid preparations of this type is described, for example, in Belgian Pat. No. 718,007.

The use of solid dyeing preparations in granulated or powder form, as stated above, is however equally practicable. Such preparations can be produced by methods which in principle are known, for example that described in French Pat. No. 1,581,900.

In the following Examples, the parts and percentages are by weight and the temperatures in degrees centigrade.

In Examples 1 to 5 the presscake of the 4-nitrotoluene-2-sulphonic acid contains, per 100 parts, 80.4 parts of 100% 4-nitrotoluene-2-sulphonic acid and 2.55 parts of sulphuric acid.

EXAMPLE 1

The dye of formula a,

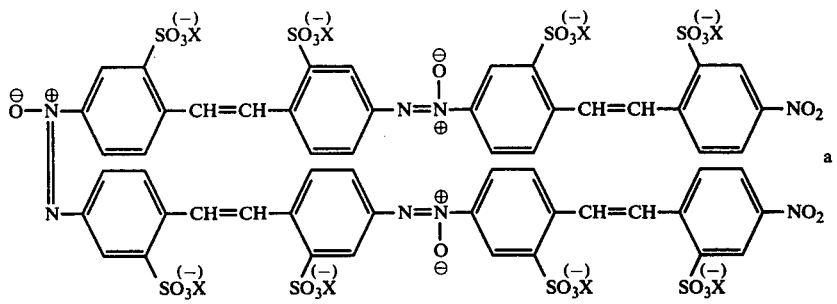

in which each X signifies N⊕(CH₃)₄ can be produced as follows.

11.9 Parts of 4-nitrotoluene-2-sulphonic acid in the form of a moist presscake are weighed out and 40 parts of 25% aqueous tetramethylammonium hydroxide solution are added dropwise. A blue-red solution forms and the temperature rises to about 45°. The solution is heated to 55° with stirring and held at this temperature for 1 hour. Afterwards the resulting red-brown suspension is cooled and neutralized with about 4.7 parts of 30% hydrochloric acid. The suspension is dried in a drying oven. 17 Parts of a reddish yellow dye of formula a are obtained.

To neutralize the condensation product, sulphuric, phosphoric, acetic or formic acid or an ammonium salt can be used in place of 30% hydrochloric acid.

EXAMPLE 2

The dye of formula b,

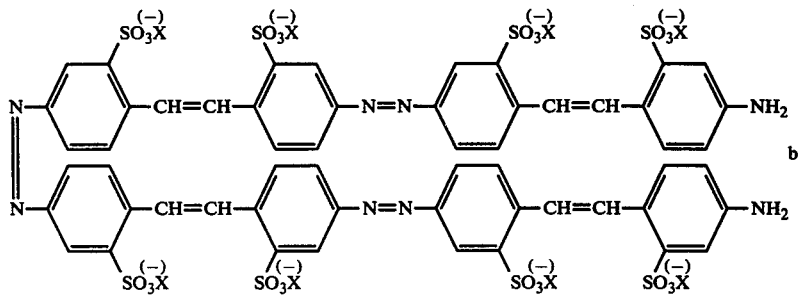

in which each X signifies the radical of the formula N⊕(CH₃)₄ can be produced as follows.

12.2 Parts of 2-nitrotoluene-2-sulphonic acid in the form of a moist filtercake are weighed out and 40 parts of a 20% tetramethyl ammonium hydroxide solution are added dropwise. The blue-red solution formed is raised to 40° with stirring and stirred for 2 hours at this temperature. Then 3.3 parts of dextrose hydrate are added and the solution stirred for 2 hours at 40°, and after this reduction the compound is precipitated from the solution. The mixture is cooled and neutralized with 2.9 parts of 30% hydrochloric acid. It is then diluted with water to 150 parts, whereupon a clear concentrated solution is obtained which contains the orange dye of formula b.

EXAMPLE 3

The dye of formula c,

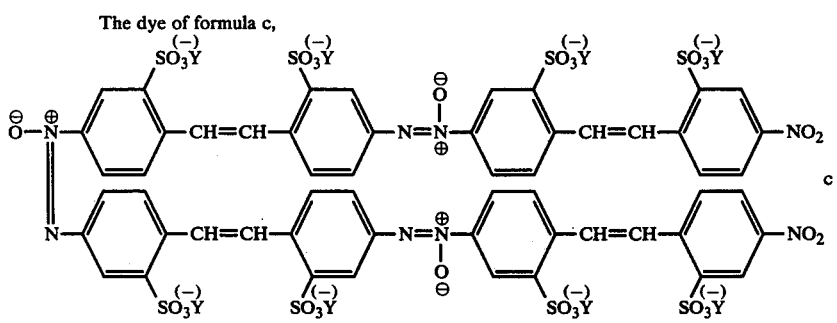

in which each Y signifies the group of the formula

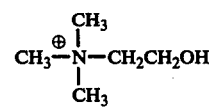

can be produced from (2-hydroxyethyl)trimethylammonium hydroxide (choline) as follows.

27.6 Parts of 4-nitrotoluene-2-sulphonic acid in the form of the moist presscake are mixed with 50 parts of water with stirring. Over 15 minutes 60 parts of a 50% aqueous choline solution are added dropwise. Subsequently the mixture is heated to 75° and held at this temperature for 1 hour. After this time 20 parts of ice are added. The cooled solution is neutralized with 11.7 parts of a 30% hydrochloric acid solution. A clear, concentrated solution is obtained which contains the reddish yellow dye of formula c.

EXAMPLE 4

The dye of formula d,

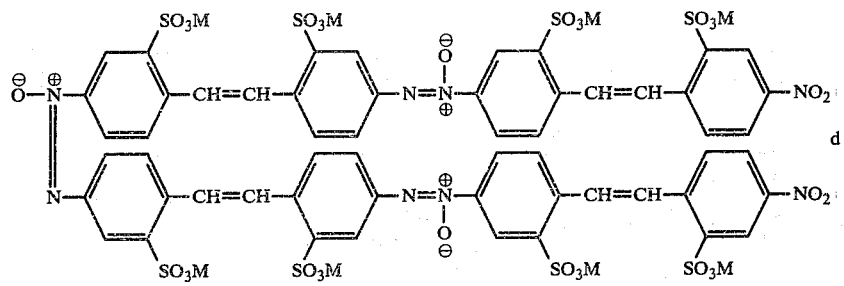

in which each M signifies sodium or tetramethylammonium in the ratio of 2.8:1 can be produced as follows.

5 Parts of the powder dye obtained as described in Example 1 are added to 35 parts of water with stirring. A clear dark red solution forms. 10 Parts of sodium chloride are added, whereupon which the dye is quantitatively precipitated. Stirring is continued for 30 minutes, after which the suspension is raised to 70° and filtered with suction. A moist presscake is obtained which contains the reddish yellow dye of formula d in which M as the sodium and the tetramethylammonium cation is present in the ratio of 2.8:1.

EXAMPLE 5

If 10 parts of ammonium, lithium or potassium chloride are used in Example 4 in place of 10 parts of sodium chloride, a moist presscake is obtained which contains the dye of formula d in which M as the ammonium, lithium or potassium cation and the tetramethylammonium cation is present in the ratio of 0.75:1.

For conversion of the tetraalkylammonium salts of the dyes a, b and c into the corresponding alkali metal or ammonium salt by the procedures of Example 4 or 5, in place of the chlorides there used, the corresponding sulphates, acetates, phosphates, etc. of the corresponding alkali metal or ammonium ion can be used. Furthermore, in place of the dextrose hydrate named as reducing agent in Example 2, an equivalent amount of an alkali metal sulphite or sulphide, glycerin, hydroxyalkylamine or aldehyde can be used.

In order to determine the ratio of the cations, the dye salt is freed from excess salt by means of dialysis, dried and the percentage ratio of the cations determined by one of the standard analytical methods (titration, gravimetry, flame spectrometry, etc.).

DYEING EXAMPLE A

A suspension of 70 parts of chemically bleached sulphite pulp (from soft wood) and 30 parts of chemically bleached sulphite pulp (from birch wood) in 2000 parts of water is beaten in a hollander beater. 0.2 Parts of the dye salt described in Example 1 are sprinkled into the suspension. After further mixing for 20 minutes the suspension is converted into absorbent paper dyed in a reddish yellow shade. The backwater is practically colourless.

DYEING EXAMPLE B 0.5 Parts of the dye salt described in Example 1 are dissolved in 100 parts of hot water. The solution is cooled to room temperature and added to a suspension of 100 parts of chemically bleached sulphite pulp in 2000 parts of water which has been beaten in a hollander beater. After mixing for 15 minutes the stock is sized. Paper made from this stock has a reddish yellow shade of medium depth which has good wet fastness properties.

DYEING EXAMPLE C

A continuous sheet of absorbent, unsized paper is conveyed at 40°-50° through a dye solution of the following composition:
  0.5 parts of the dye salt described in Example 1,
  0.5 parts of starch and
  99.0 parts of water.

The excess dye solution is expressed by a pair of rollers. The dried sheet is dyed in a reddish yellow shade.

In Examples 6 to 9, the presscake of the 4-nitrotoluene-2-sulphonic acid used as starting material contains, per 135 parts, 108.5 parts of 100% 4-nitrotoluene-2-sulphonic acid and 3.45 parts of sulphuric acid.

EXAMPLE 6

A salt of the dye of formula a',

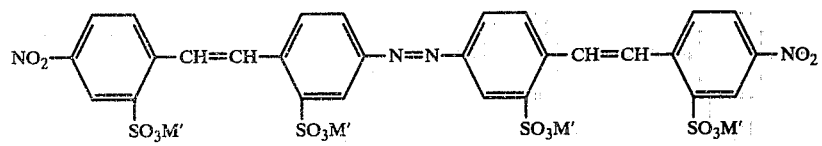

in which M' signifies ammonium and lithium cations in a ratio of approximately 2:1,
can be produced as follows.

A moist presscake of 135 parts of 4-nitrotoluene-2-sulphonic acid is mixed with 150 parts of water. In 15 minutes 52.5 parts of lithium hydroxide monohydrate are gradually added, which causes a temperature increase to 50° and darkens the colour of the solution. The temperature is increased further to 60°-65° and the solution stirred for 1 hour. Then 100 parts of ice and 200 parts of cold water are added. The orange paste formed is adjusted to pH 7 with 70 parts of 30% hydrochloric acid, the temperature increased to 75°-80° and 100 parts of ammonium chloride entered in 30 minutes. This temperature is maintained for 1 hour, after which common salt is added and the suspension is filtered with suction. 320 Parts of a moist presscake are obtained which contains the greenish yellow dye of formula a', in which M' as the ammonium and lithium cations is present in the ratio of approximately 2:1. To neutralize the condensation product, sulphuric, phosphoric, acetic or formic acid or an ammonium salt can be used in place of 30% hydrochloric acid.

EXAMPLE 7

A salt of the dye of formula b',

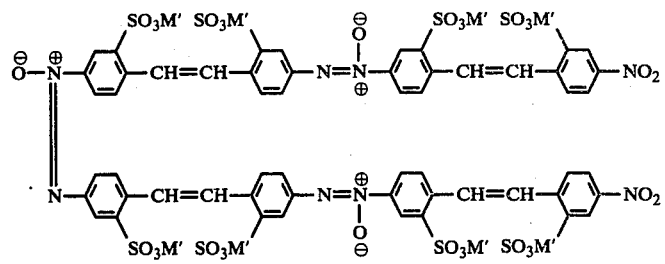

in which M' is as defined in Example 6, can be produced as follows.

135 Parts of 4-nitrotoluene-2-sulphonic acid in the form of a moist presscake are mixed with 150 parts of water and heated to 50° with continued stirring. In 15 minutes 52.5 parts of lithium hydroxide monohydrate are gradually added, whereupon the temperature of the solution increases to 60° and its colour darkens. In 30 minutes the temperature is increased to 75° and this temperature is maintained for 2 hours with continued stirring. At this point 100 parts of ice and 200 parts of cold water are added. Stirring is continued for 1 hour, then the cooled suspension is adjusted to pH 7 with 60 parts of 30% hydrochloric acid. The temperature is increased to 75°–80° and in 30 minutes 100 parts of ammonium chloride are added, after which stirring is continued at the same temperature for 1 hour. The reaction mixture is salted out and the precipitate is filtered with suction. 370 Parts of a moist presscake are obtained which contains the reddish yellow dye of formula b', in which M' as the ammonium and lithium caton is present in the ratio of 2:1.

EXAMPLE 8

320 Parts of the moist presscake obtained as described in Example 7 are stirred in 500 parts of water until a fine suspension is formed. The suspension is heated to 75° and in 5 minutes 100 parts of ammonium chloride are added. Stirring is continued for 1 hour at 75°, then the suspension is salted out and is filtered with suction. 250 Parts of a moist presscake are obtained which contains the reddish yellow dye of formula b', in which M' as the ammonium and lithium cation is present in the ratio of 6:1.

If the above presscake is again suspended and precipitated in the same manner, a moist presscake is obtained which contains the dye of formula b' in which M' is present as the ammonium and lithium cation in the ratio of approximately 16:1, i.e. virtually all the —$SO_3H$ groups are present in ammonium salt form.

EXAMPLE 9

An ammonium salt of the dye of formula c',

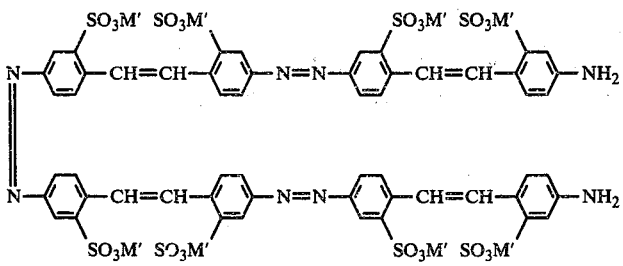

in which M' is as defined in Example 6, can be produced as follows.

135 Parts of 4-nitrotoluene-2-sulphonic acid in the form of a moist presscake are mixed with 150 parts of water with stirring and then heated to 50°. In 15 minutes 52.5 parts of lithium hydroxide monohydrate are entered, in 30 minutes the temperature is raised to 75° and this temperature held for 2 hours with continued stirring. 75 Parts of dextrose hydrate are added slowly so that the temperature does not exceed 80°. Stirring is continued for 2 hours at 75°–80°, then 400 parts of water are added for cooling, the solution neutralized with 17 parts of 30% hydrochloric acid and diluted to 1.5 liters. 300 Parts of ammonium chloride are added at 75°–80°, and this temperature is maintained for 2 hours. Subsequent filtration after salting out with suction gives 230 parts of a moist presscake which contains the orange dye of formula c' in which M' as the ammonium and lithium cation is present in the ratio of 2:1.

The ammonium chloride used in Examples 6 to 9 to convert the lithium salts into the corresponding ammonium salts of the specified dyes can be replaced by the equivalent amount of ammonium sulphate, ammonium acetate or ammonium phosphate.

To determine the quantitative ratio of the cations, the dye is freed from excess salt by dialysis, dried and the percentage ratio of the cations determined by one of the standard analytical methods (titration, gravimetry, flame spectrometry, etc).

In place of the dextrose hydrate used in Example 9, an equivalent amount of alkali metal sulphite or sulphide, glycerin, hydroxyalkylamine or a suitable aldehyde can be used as reducing agent.

DYEING EXAMPLE D

A suspension of 70 parts of chemically bleached sulphite pulp (from soft wood) and 30 parts of chemically bleached sulphate pulp (from birch wood) in 2000 parts of water is beaten in a hollander beater. 0.2 Parts of the dye salt described in Example 6 are sprinkled into the suspension. After further mixing for 20 minutes, the suspension is converted into absorbent paper dyed in a greenish yellow shade. The backwater is practically colourless.

DYEING EXAMPLE E 0.5 Parts of the dye salt described in Example 6 are dissolved in 100 parts of hot water. The solution is cooled to room temperature and added to a suspension of 100 parts of chemically bleached sulphite pulp in 2000 parts of water which has been beaten in a hollander beater. After mixing for 15 minutes the stock is sized. Paper made from this stock has a greenish yellow shade of medium depth which has good wet fastness properties.

DYEING EXAMPLE F

A continuous sheet of absorbent, unsized paper is conveyed at 40°–50° through a dye solution of the following composition:
 0.5 parts of the dye salt described in Example 6,
 0.5 parts of starch and
 99.0 parts of water.

The excess dye solution is expressed by a pair of rollers.

The dried sheet is dyed in a greenish yellow shade.

In Examples 10 to 15 the presscake of the 4-nitrotoluene-2-sulphonic acid contains, per 100 parts, 92.5 parts of 100% 4-nitrotoluene-2-sulphonic acid in the form of its ammonium salt.

EXAMPLE 10

The ammonium salt of 4-nitrotoluene-2-sulphonic acid can be produced as follows.

500 Parts of an acid presscake containing 394 parts of 100% 4-nitrotoluene-2-sulphonic acid and 3 parts of sulphuric acid are entered into 1200 parts of water and dissolved with stirring. Approximately 250 parts of a 24% ammonium hydroxide solution are added dropwise to the solution, which causes almost quantitative precipitation of the ammonium salt of 4-nitrotoluene-2-sulphonic acid. The pH of the suspension is adjusted exactly to 7 and the temperature is increased to 85°–90° with stirring. As soon as everything is dissolved, the solution is allowed to cool to 15°. The ammonium salt of 4-nitrotoluene-2-sulphonic acid settles out in the form of fine needles and can be satisfactorily filtered with the application of vacuum. 424 Parts of a neutral presscake are obtained which contains 392 parts of the 100% ammonium salt of 4-nitrotoluene-2-sulphonic acid.

EXAMPLE 11

The dye of formula $a''$,

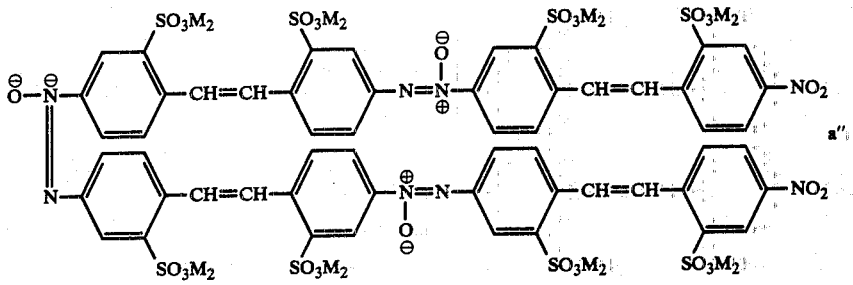

can be produced as follows:

A moist presscake of 170 parts of the ammonium salt of 4-nitrotoluene-2-sulphonic acid produced as in Example 10 is stirred into 300 parts of water, after which 58.5 parts of lithium hydroxide monohydrate are added. The temperature is increased to 50°–55° and this temperature maintained for 12 hours. The suspension formed is cooled to about 20°, then 126 parts of 30% hydrochloric acid are added dropwise in 1 hour 30 minutes, by which time pH 7 is reached. Stirring is continued for 1 hour and the product filtered off with vacuum. 400 Parts of a moist presscake are obtained which contains the reddish yellow dye of formula $a''$ in which $M_2$ as the ammonium and lithium cation is present in the ratio of 1:1.4. Sulphuric, phosphoric, acetic or formic acid can be used in place of 30% hydrochloric acid to neutralize the condensation product.

EXAMPLE 12

The dye of formula $b''$,

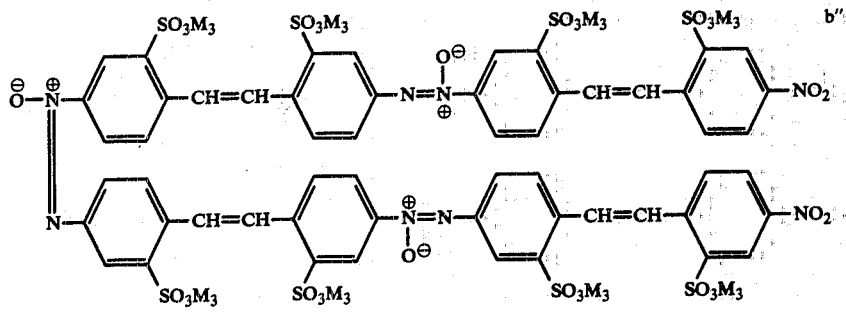

can be produced as follows:

A moist presscake of 127 parts of the ammonium salt of 4-nitrotoluene-2-sulphonic acid produced as in Example 10 is stirred into 100 parts of water, after which 133 parts of 30% sodium hydroxide solution are added dropwise. The temperature is increased to 50°–55° and this temperature maintained for 12 hours. The suspension formed is cooled, neutralized to pH 7 with 115 parts of 30% hydrochloric acid and stirred for a further hour. The product is then filtered off with suction. 290 Parts of a moist presscake are obtained which contains the reddish yellow dye of formula b" in which $M_3$ as the ammonium and sodium cation is present in the ratio of 1:2.5. To neutralize the condensation product, sulphuric, phosphoric, acetic or formic acid can be used in place of 30% hydrochloric acid.

EXAMPLE 13

The dye of formula c",

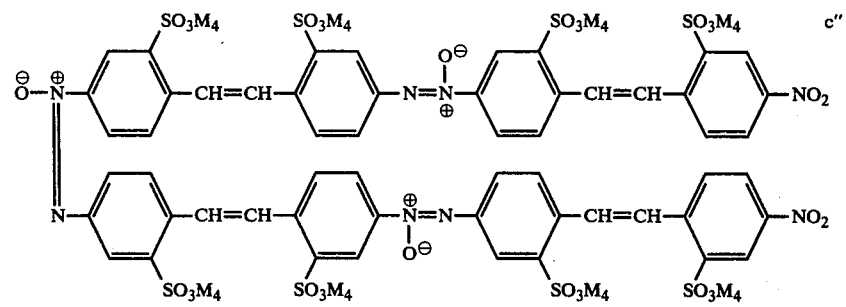

can be produced as follows:

A moist presscake of 112 parts of the ammonium salt of 4-nitrotoluene-2-sulphonic acid produced as in Example 10 is stirred into 150 parts of water, after which 200 parts of tetramethylammonium hydroxide 40% are added dropwise. The temperature is increased to 50°–55° and this temperature is maintained for 12 hours. The resulting suspension is cooled to about 20°, neutralized to pH 7 with 190 parts of 30% hydrochloric acid and then set with 300 parts of iso-propyl alcohol. Stirring is continued for 1 hour and the product filtered off with vacuum. 115 Parts of a moist presscake are obtained which contains the reddish yellow dye of formula c" in which $M_4$ as the ammonium and tetramethylammonium cation is present in the ratio of about 1:4.8. To neutralize the condensation product, sulphuric, phosphoric, acetic or formic acid can be used in place of 30% hydrochloric acid.

EXAMPLE 14

The dye of formula d",

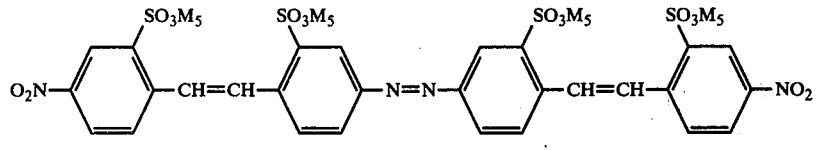

can be produced as follows:

A moist presscake of 127 parts of the ammonium salt of 4-nitrotoluene-2-sulphonic acid produced as in Example 10 is stirred into 150 parts of water, after which 44 parts of lithium hydroxide monohydrate are added. The temperature is increased to 50°–55° and this temperature maintained for 2 hours. The suspension formed is cooled to 20°. In 90 minutes 120 parts of 30% hydrochloric acid are dropped carefully into the suspension, by which time the pH reaches 7. Stirring is continued for 1 hour, then the product is isolated by filtration with suction. 180 Parts of a moist presscake are obtained which contains the greenish yellow dye of formula d" in which $M_5$ as ammonium and lithium cation is present in the ratio of 1:2.2. In place of 30% hydrochloric acid, sulphuric, phosphoric, acetic or formic acid can be used to neutralize the condensation product.

EXAMPLE 15

The dye of formula e",

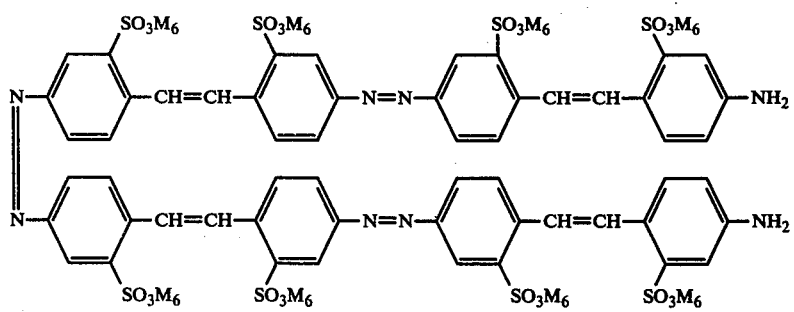

can be produced as follows:

A moist presscake of 127 parts of the ammonium salt of 4-nitrotoluene-2-sulphonic acid produced as in Example 10 is stirred into 150 parts of water, after which 44 parts of lithium hydroxide monohydrate are added. The temperature is increased to 50°–55° and this temperature maintained for 12 hours. Then 40 parts of dextrose hydrate are gradually added in 30 minutes. Stirring is continued for 5 hours at 50°-55°, the resulting suspension cooled and neutralized to pH 7 with 55 parts of 30% hydrochloric acid. 500 Parts of iso-propyl alcohol are run into the suspension and stirring continued for 1 hour. The product is then filtered with suction. 400 Parts of a moist presscake are obtained which contains the orange dye of formula e'' in which $M_6$ as the ammonium and lithium cation is present in the ratio of 1:2.7. In place of 30% hydrochloric acid, sulphuric, phosphoric, acetic or formic acid can be used to neutralize the condensation product. In place of dextrose hydrate, an equivalent amount of an alkali metal sulphite or sulphide, glycerin, hydroxyalkylamine or an aldehyde can be used as the reducing agent.

To determine the quantitative ratio of the cations, the dye is freed from excess salt by dialysis, dried and the percentage ratio of the cations determined by one of the standard methods of analysis (e.g. titration, gravimetry or flame spectrometry).

DYEING EXAMPLE G

A suspension of 70 parts of chemically bleached sulphite pulp (from soft wood) and 30 parts of chemically bleached sulphate pulp (from birch wood) in 2000 parts of water is beaten in a hollander beater. 0.2 Parts of the dye salt produced in Example 11 are sprinkled into the suspension. After further mixing for 20 minutes, the suspension is converted into absorbent paper dyed in a reddish yellow shade. The backwater is practically colourless.

DYEING EXAMPLE H 0.5 Parts of the dye salt produced in Example 11 are dissolved in 100 parts of hot water. The solution is cooled to room temperature and added to a suspension of 100 parts of chemically bleached sulphite pulp in 2000 parts of water which has been beaten in a hollander beater. After mixing for 15 minutes, the stock is sized. Paper made from this stock has a reddish yellow shade of medium depth which shows good wet fastness properties.

DYEING EXAMPLE I

A continuous sheet of absorbent, unsized paper is conveyed at 40°-50° through a dye solution of the following composition:
0.5 parts of the dye salt produced in Example 11,
0.5 parts of starch, and
99.0 parts of water.

The excess dye solution is expressed by a pair of rollers. The dried sheet is dyed in a reddish yellow shade.

The dye salts produced in Examples 12 to 15 can also be used in similar manner to the dye salt produced in Example 11, in the above Dyeing Examples G to I.

What is claimed is:

1. A process for the production of a stilbene-azo or stilbene-azoxy dye, or a mixture of such dyes, comprising condensing a compound of the formula

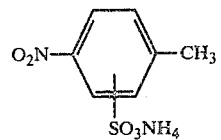

in the presence of a tetra(alkyl or substituted alkyl)ammonium or alkali metal hydroxide, whereby a stilbene-azo or stilbene-azoxy dye containing at least one sulfo group per molecule wherein at least one cation per molecule is ammonium and every other cation is independently a tetra(alkyl or substituted alkyl)ammonium or alkali metal cation, or a mixture of such dyes, is produced.

2. A process according to claim 1 for the production of a stilbene-azo or stilbene-azoxy dye, or a mixture of such dyes, comprising condensing a compound of the formula

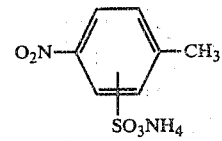

in the presence of a tetra($C_{1-6}$alkyl or $C_{1-6}$alkyl substituted by cyano, halo or hydroxy)ammonium, lithium, sodium or potassium hydroxide, whereby a stilbene-azo or stilbene-azoxy dye containing at least one sulfo group per molecule wherein at least one cation per molecule is ammonium and every other cation is independently a tetra($C_{1-6}$alkyl or $C_{1-6}$alkyl substituted by cyano, halo or hydroxy)ammonium, lithium, sodium or potassium cation, or a mixture of such dyes, is produced.

3. A process according to claim 2 wherein said condensation is effected in water.

4. A process according to claim 3 wherein said condensation is effected at a pH of 11 to 14.

5. A process according to claim 2 wherein said condensation is effected at a temperature of 45° to 65° C.

6. A process according to claim 2 wherein said compound of the formula

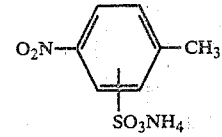

is ammonium 4-nitrotoluene-2-sulfonate.

7. A process according to claim 6 comprising condensing ammonium 4-nitrotoluene-2-sulfonate in the presence of a tetra($C_{1-6}$alkyl or $C_{1-6}$alkyl monosubstituted by cyano, halo or hydroxy)ammonium, lithium, sodium or potassium hydroxide in an aqueous medium at a pH of 7.5 to 14 and a temperature of about 30° to 80° C., whereby a stilbene-azo or stilbene-azoxy dye having at least one ammonium cation per molecule and every other cation of which is a tetra($C_{1-6}$alkyl or $C_{1-6}$alkyl monosubstituted by cyano, halo or hydroxy)ammonium, lithium, sodium or potassium cation, or a mixture of such dyes, is produced.

8. A process according to claim 7 wherein the condensation is effected at a temperature of 30° to 75° C.

9. A process according to claim 8 wherein the condensation is effected for about 1 to 12 hours at a pH of 11 to 13 and a temperature of 45° to 65° C. and the mol ratio of tetra($C_{1-6}$alkyl or $C_{1-6}$alkyl monosubstituted by cyano, halo or hydroxy)ammonium, lithium, sodium or potassium hydroxide to ammonium 4-nitrotoluene-2-sulfonate is 0.8 to 4:1.

10. A process according to claim 7 wherein the condensation is effected for about 1 to 12 hours at a temperature of about 50° to 80° C. and a pH of 12 to 14 and the mol ratio of tetra($C_{1-6}$alkyl or $C_{1-6}$alkyl monosubstituted by cyano, halo or hydroxy)ammonium, lithium, sodium or potassium hydroxide to ammonium 4-nitrotoluene-2-sulfonate is about 1 to 6:1.

11. A process according to claim 7 comprising condensing ammonium 4-nitrotoluene-2-sulfonate in the presence of a tetra($C_{1-3}$alkyl or $C_{1-3}$alkyl monosubstituted by cyano, chloro, bromo or hydroxy)ammonium, lithium, sodium or potassium hydroxide in an aqueous medium for about 1 to 12 hours at a temperature of 45° to 65° C. and a pH of 11 to 13 wherein the mol ratio of tetra($C_{1-3}$alkyl or $C_{1-3}$alkyl monosubstituted by cyano, chloro, bromo or hydroxy)ammonium, lithium, sodium or potassium hydroxide to ammonium 4-nitrotoluene-2-sulfonate is 0.8 to 4:1.

12. A process according to claim 11 comprising condensing ammonium 4-nitrotoluene-2-sulfonate in the presence of tetramethylammonium, lithium or sodium hydroxide in water for about 1 to 12 hours at a temperature of 45° to 65° C. and a pH of 11 to 13 wherein the mol ratio of tetramethylammonium, lithium or sodium hydroxide to ammonium 4-nitrotoluene-2-sulfonate is 0.8 to 4:1.

13. A process according to claim 2 wherein simultaneous or subsequent reduction is effected, whereby a stilbene-azo dye in mixed salt form having at least one amino group per molecule and at least one ammonium cation per molecule is produced.

14. A process according to claim 2 wherein said stilbene-azo or stilbene-azoxy dye is a dye of the formula

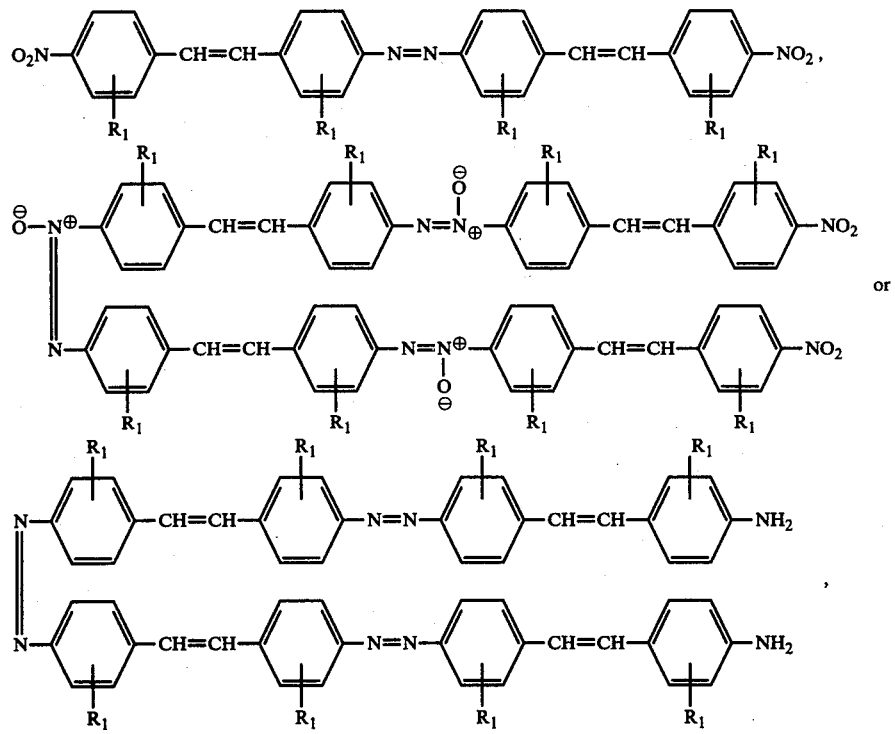

wherein each $R_1$ is —$SO_3M'$,
wherein each M' is independently ammonium, tetra($C_{1-6}$alkyl or $C_{1-6}$alkyl monosubstituted by hydroxy, cyano or halo)ammonium, lithium, sodium or potassium, with the proviso that at least one M' per molecule is ammonium.

15. A process according to claim 14 wherein said stilbene-azo or stilbene-azoxy dye is a dye of the formula

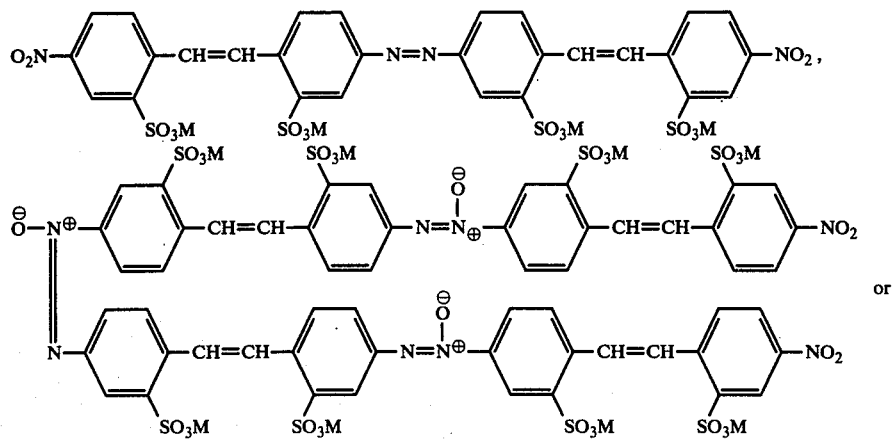

-continued

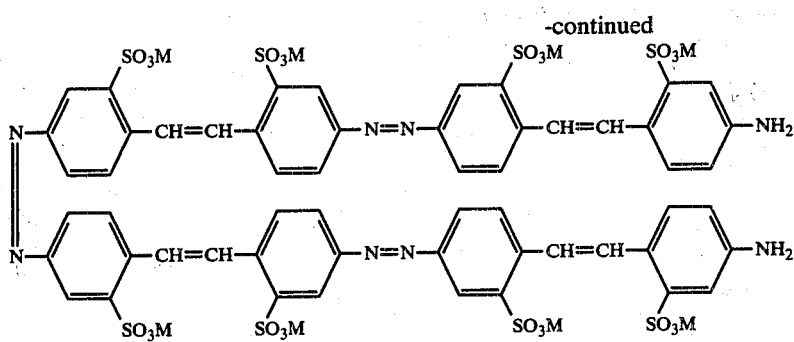

wherein each M is ammonium, tetra(C$_{1-3}$alkyl)ammonium, lithium, sodium or potassium, with the proviso that at least one M per molecule is ammonium.

16. A process according to claim 2 comprising condensing a compound of the formula

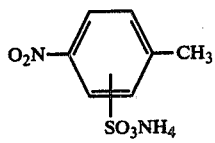

in the presence of tetramethylammonium hydroxide, whereby a stilbene-azo or stilbene-azoxy dye in mixed tetramethylammonium/ammonium salt form having at least one ammonium cation per molecule is produced.

17. A process according to claim 16 wherein said compound of the formula

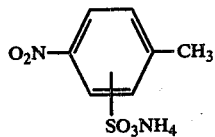

is ammonium 4-nitrotoluene-2-sulfonate.

18. A process according to claim 2 comprising condensing a compound of the formula

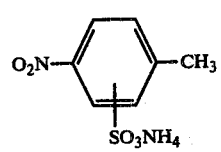

in the presence of lithium hydroxide, whereby a stilbene-azo or stilbene-azoxy dye in mixed lithium/ammonium salt form having at least one ammonium cation per molecule is produced.

19. A process according to claim 18 wherein said compound of the formula

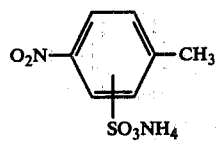

is ammonium 4-nitrotoluene-2-sulfonate.

20. A process according to claim 19 comprising condensing ammonium 4-nitrotoluene-2-sulfonate in the presence of lithium hydroxide in an aqueous medium at a pH of 7.5 to 14 and a temperature of 30° to 75° C., whereby a stilbene-azo or stilbene-azoxy dye in mixed lithium/ammonium salt form having at least one ammonium cation per molecule is produced.

21. A process according to claim 20 wherein the condensation is effected for about 1 to 12 hours at a pH of 11 to 13 and a temperature of 45° to 65° C. and the mol ratio of lithium hydroxide to ammonium 4-nitrotoluene-2-sulfonate is 0.8 to 4:1.

22. A process according to claim 20 wherein the condensation is effected at a temperature of 50° to 55° C. for 12 hours and the mol ratio of lithium hydroxide to ammonium 4-nitrotoluene-2-sulfonate is about 2:1.

23. A process according to claim 18 wherein said stilbene-azo or stilbene-azoxy dye is a dye of the formula

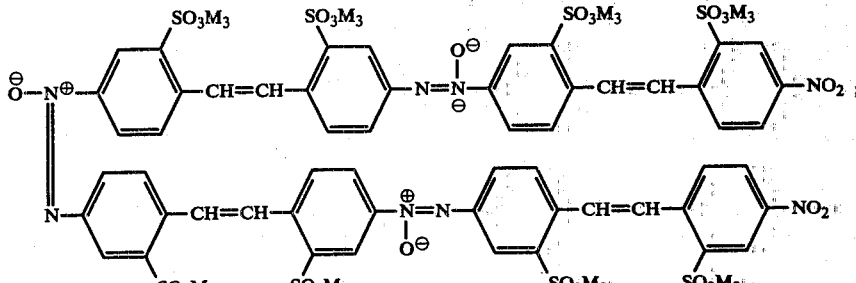

wherein each M$_3$ is independently ammonium or lithium, with the proviso that the ratio of ammonium to lithium cations is approximately 1:1.4.

24. A process according to claim 2 comprising condensing a compound of the formula

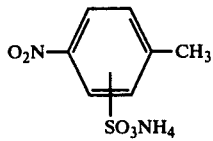
in the presence of sodium hydroxide, whereby a stilbene-azo or stilbene-azoxy dye in mixed sodium/ammonium salt form having at least one ammonium cation per molecule is produced.
25. A process according to claim 24 wherein said compound of the formula
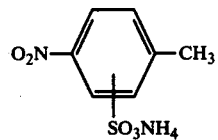
is ammonium 4-nitrotoluene-2-sulfonate.
* * * * *